United States Patent [19]

Kato et al.

[11] Patent Number: 4,827,909

[45] Date of Patent: May 9, 1989

[54] ENDOSCOPIC APPARATUS

[75] Inventors: Haruo Kato, Kuroiso; Satoshi Saito, Nasu, both of Japan

[73] Assignee: Kabushiki Kaisha Toshiba, Kawasaki, Japan

[21] Appl. No.: 175,285

[22] Filed: Mar. 30, 1988

[30] Foreign Application Priority Data

Mar. 31, 1987 [JP] Japan .................................. 62-75877

[51] Int. Cl.⁴ ............................................... H04N 7/18
[52] U.S. Cl. ........................................... 128/6; 358/98
[58] Field of Search ................................ 128/6; 358/98

[56] References Cited

U.S. PATENT DOCUMENTS 4,259,948 4/1981 Urban .................................... 358/98
4,651,201 3/1987 Schoolman ........................... 358/98

Primary Examiner—Leo P. Picard
Attorney, Agent, or Firm—Foley & Lardner, Schwartz, Jeffery, Schwaab, Mack, Blumenthal & Evans

[57] ABSTRACT

An endoscopic apparatus comprises a plurality of illuminating members disposed at an end of a scope around an observing point and illuminating an inspected object by sequentially switching illuminating light from positions different from each other; an image pick-up device disposed at the observing point and picking up an image of the inspected object illuminated by sequentially switching the plural illuminating members; and a processing unit for processing image information outputted from the image pick-up device and corresponding to the respective positions of the plural illuminating members. The processing unit outputs information with respect to the height of the inspected object having a three-dimensional shape.

12 Claims, 4 Drawing Sheets

ENDOSCOPIC APPARATUS

The present invention relates to an endoscopic apparatus for measuring irregularity of a diseased portion within a human's body.

BACKGROUND OF THE INVENTION

A conventional endoscopic apparatus for measuring the size of a diseased portion within a human's body is disclosed in Gastroenterological Endoscopy, Vol. (25) 6, p. 868, published in June 1983 where two-dimensional diffracted spot light provided when laser beam is diffracted by a fiber diffraction grating of a penetrating type is projected onto an inspected object to obtain predetermined information with respect to the measurement.

In this conventional example, a predetermined clearance is disposed between an arranged place of the fiber diffraction grating at an end of a scope, and an observing point where an objective lens, an image pick-up element, etc., are disposed. When the two-dimensional diffracted spot light diffracted by the fiber diffraction grating is projected on the inspected object and a projected image is observed from the observing point, a change corresponding to the shape of the inspected object is generated in the clearance between the spot light projected onto the inspected object. The distance between the observing point and the inspected object such as a diseased portion, and the size thereof are measured to obtain information about the situation and extension of irregularity of the diseased portion.

However, in this conventional example, the irregularity of the diseased portion is not exactly measured three-dimensionally, and cannot be displayed on a monitor, etc., at real time.

A second conventional example is disclosed in "restoration of the shape and position information of a three-dimensional object by an illuminance difference stereo-method" of Vol. J69-D, No. 3. pp 427–433, written by Ko, Kawashima, and Aoki published by Singakuron on March, 1986. In this method, the shape of the three-dimensional object can be restored by using a difference in illumination intensity.

However, in this second conventional example, the distance is treated as a known parameter, and only a principle of the restoration technique is disclosed, thereby providing no solution with respect to a detailed technique for applying to an endoscope the measurement of irregularity of a diseased portion with a human's body.

SUMMARY OF THE INVENTION

With the problems mentioned above, an object of the present invention is to provide an endoscopic apparatus for exactly measuring irregularity of an inspected object such as a diseased portion within a body three-dimensionally and displaying the diseased portion on a monitor, etc., at real time.

With the above object in view, the present invention resides in an endoscopic apparatus comprising a plurality of illuminating means disposed at an end of a scope around an observing point and illuminating an inspected object by sequentially switching illuminating light from positions different from each other; image pick-up means disposed at the observing point and picking up an image of the inspected object illuminated by sequentially switching the plural illuminating means; and processing means for processing image information outputted from the image pick-up means and corresponding to the respective positions of the plural illuminating means, said processing means outputting information with respect to the height of the inspected object having a three-dimensional shape.

BRIEF DESCRIPTION OF THE DRAWINGS

The present invention will be more apparent from the following description of the preferred embodiments thereof in conjunction with the accompanying drawings in which.

DETAILED DESCRIPTION OF THE PREFERRED EMBODIMENTS

The preferred embodiments of the present invention will now be described in detail with reference to the accompanying drawings.

Figure 1:
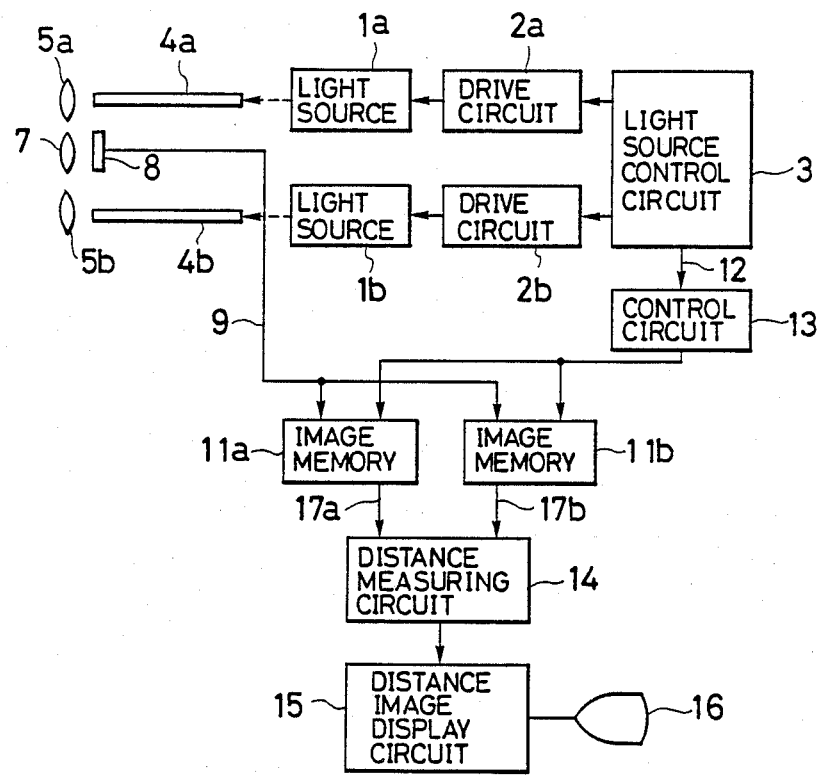
FIG. 1 is a block view showing the whole construction of an endoscopic apparatus in accordance with one embodiment of the present invention.
Figure 2:
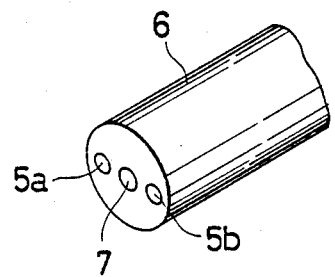
FIG. 2 is a view showing the construction of a scope end of the endoscopic apparatus.

FIGS. 1 and 2 show the whole construction of an endoscopic apparatus in accordance with one embodiment of the present invention. A first light source 1a and a second light source 1b are respectively connected to a light source control circuit 8 through drive circuits 2a and 2b, which constitute a means for switching illuminated light. A scope 6 to be inserted into a human's body is constituted by a light guide 4a of illuminated light from the first light source 1a, a light guide 4b of illuminated light from the second light source 1b, output signal lines connected to a charge coupled device described later, etc., which are integrally disposed. A first illuminating lens 5a and a second illuminating lens 5b as an illuminating means are disposed on both sides of an observing point or window at an end of the scope 6. A projecting end of the light guide 4a faces the rear side of the first illuminating lens 5a, and a projecting end of the light guide 4b faces the rear side of the second illuminating lens 5b.

A charge coupled device 8 composed of an objective lens 7 and a solid image pick-up element as an image pick-up means is disposed at the observing point. As shown in FIG. 2, the first and second illuminating lenses 5a and 5b and the objective lens 7 are disposed at an end of the scope 6. The endoscope in this embodiment is constituted as an endoscope of a front viewing type, and is provided with insertion ports, etc., which are not illustrated in the drawings.

An output signal line 9 of the charge coupled device 8 is connected to a first image memory 11a and a second image memory 11b which are connected through a control circuit 13 to a signal line 12 for a synchronous signal from the light source control circuit 3. The write timing of the first and second image memories 11a and 11b is controlled by a control signal from the control circuit 13, and the first and second image memories 11a and 11b memorize image information corresponding to the first and second illuminating lenses 5a and 5b picked up by the charge coupled device 8.

Output terminals of the first and second image memories 11a and 11b are commonly connected to a distance measuring circuit 14 as a processing means. An output terminal of the distance measuring circuit 14 is connected to a monitor 16 through a distance image display circuit 15.

The internal construction of the distance measuring circuit 14 will be described in more detail with reference to FIG. 3.

Figure 3:
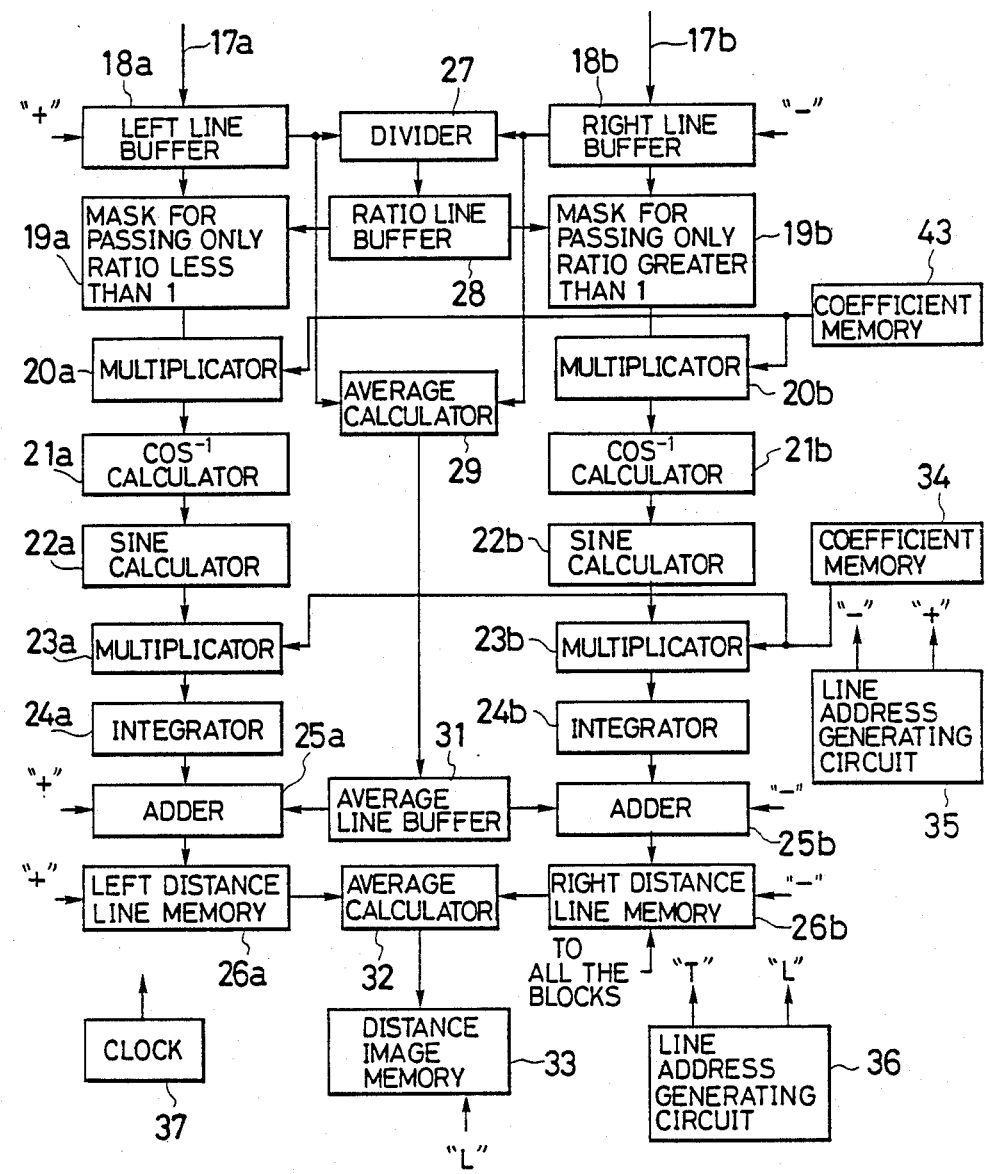
FIG. 3 is a block view showing the construction of a distance measuring circuit in the whole construction of the endoscopic apparatus.

The distance measuring circuit 14 has internal circuits respectively corresponding to the first and second image memories 11a and 11b and symmetrical with respect to the right and left of FIG. 3. The internal circuit corresponding to the first image memory 11a has a left line buffer 18a connected to an output line 17a of the first image memory 11a, a mask device 19a connected to the left line buffer 18a and outputting a signal only when a ratio described later is less than one, a multiplicator 20a connected to the mask device 19a, a $\cos^{-1}$ calculator 21a connected to the multiplicator 20a, a sine calculator 22a connected to the $\cos^{-1}$ calculator 21a, a multiplicator 23a connected to the sine calculator 22a, an integrator 24a connected to the multiplicator 23a, an adder 25a connected to the integrator 24a, and a left-distance line-memory 26a connected to the adder 25a.

The internal circuit corresponding to the second image memory 11b, as well as the internal circuit corresponding to the first image memory 11a, has a right line buffer 18b connected to an output line 17b of the second image memory 11b, a mask device 19b connected to the right line buffer 18b and outputting a signal only when a ratio described later is greater than one, a multiplicator 20b connected to the mask device 19b, a $\cos^{-1}$ calculator 21b connected to the multiplicator 20b, a sine calculator 22b connected to the $\cos^{-1}$ calculator 21b, a multiplicator 23b connected to the sine calculator 22b, an integrator 24b connected to the multiplicator 23b, an adder 25b connected to the integrator 24b, and a right distance line memory 26b connected to the adder 25b.

The distance measuring circuit 14 further has a divider 27, a ratio line buffer 28, a first average calculator 29, an average line buffer 31, a second average calculator 32, and a distance image memory 33. Data stored in the distance image memory 33 are supplied to the distance image display circuit 15. The distance measuring circuit 14 further has coefficient memories 34 and 43, a circuit 35 for generating addresses within a line, a circuit 36 for generating line addresses, and a generator 37 for generating a clock signal.

The operation of the apparatus mentioned above will next be described with reference to FIG. 4.

Figure 4A:
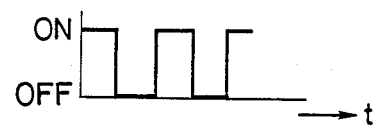
FIGS. 4A and 4B show timing charts showing illuminating timing of illuminating light switched from two illuminating devices.
Figure 4B:
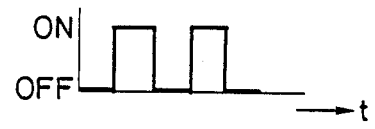

When the scope 6 is inserted into a predetermined portion within a human's body and an unillustrated three-dimensional display switch is turned on, it rises to a stereo-illuminating mode so that the first and second light sources 1a and 1b are alternately turned on and off by the control of the light source control circuit 3. Accordingly, as shown in FIGS. 4A and 4B, an inspected object is alternately illuminated by the light illuminated from the first and second illuminating lenses 5a and 5b. Such a stereo-illumination from the two different illuminated positions generates distribution of the shape of shade and intensity of the reflected light corresponding to an incident angle of the illuminated light with respect to the inspected object when the distance between the observed point and the inspected object is constant. An image provided by this stereo-illumination is picked up by the charge coupled device 8, and first image data at the illuminating time from the first illuminating lens 5a are memorized in the first image memory 11a by the control of the write timing of the control circuit 13. Second image data at the illuminating time from the second illuminating lens 5b are memorized in the second image memory 11b.

The first and second image data are processed by the distance measuring circuit 14 as follows.

The line address generating circuit 35 generates addresses for scanning respective line buffers from the left to the right with respect to "+" address, and from the right to the left with respect to "−" address, by a timing signal "T" from the line address generating circuit 36.

By the "+" address, the first image data are shifted every one picture element from the left to the right with respect to the left line buffer 18a. By the "−" address, the second image data are shifted every one picture element from the right to the left with respect to the right line buffer 18b. In the divider 27, data outputted from the left line buffer 18a are divided by data outputted from the right line buffer 18b. When the divided value is greater than one, it shows a face inclined to the right which means a state in which the right hand side of the inspected object is farther from the observing point than the left hand side thereof, and when the divided value is less than one, it shows a face inclined to the left which means a state in which the left hand side of the inspected object is farther from the observing point than the right hand side thereof.

The divided data of the divider 27 are transmitted to the ratio line buffer 28. With respect to only points in which data within the ratio line buffer 28 are greater than one, the data from the right line buffer 18b are multiplied by a coefficient provided by the coefficient memory 43 through the multiplicator 20b, thereby calculating an inclination angle by calculating $\cos^{-1}$ of the coefficient multiplied data by the $\cos^{-1}$ calculator 21b. Next, a sine value with respect to the angle data is calculated by the sine calculator 22b. The values with respect to the other points are set to be zero.

The sine value calculated by the sine calculator 22b is multiplied by a constant coefficient by the multiplicator 23b. This constant coefficient is a value for determining whether the size of a three-dimensional image displayed on the monitor 16 is increased or decreased. When the coefficient value is small, the size of the image is small, and when the coefficient value is great, the size of the image is large.

With respect to the data on the side of the right line buffer 18b thus calculated, by the "−" address, an integration is performed by the integrator 25b in a direction in which the addresses are reduced from the right to the left, and the integrated data are added by the adder 25b to data from the average line buffer 31 so that the added results are memorized in the right distance line memory 26b.

With respect to the data on the side of the left line buffer 18a, a calculation similar to the above calculation is performed with respect to only points in which data within the ratio line buffer 28 are less than one. Thereafter, by the "+" address, an integration is performed by the integrator 24a in a direction in which the addresses are increased from the left to the right, and the integrated data are added by the adder 25a to data from the average line buffer 31 so that the added results are memorized in the left distance line memory 26a.

Next, the respective stored data within the right and left distance line memories 26a and 26b are averaged by the second average calculator 32 so that the distance image data are sequentially memorized in the distance image memory 33. An unbalance in illumination intensity with respect to the right and left of an image within the screen is cancelled by the symmetrical calculation with respect to the right and left, thereby providing exact distance image data.

Thereafter, the distance image data memorized in the distance image memory 33 are sequentially outputted, and such an image is displayed on the monitor 16 through the distance image display circuit 15 as an image having illumination intensity corresponding to the contour or height of the inspected object. Thus, the information with respect to the height in irregularity of the inspected object are three-dimensionally provided at real time.

Figure 5:
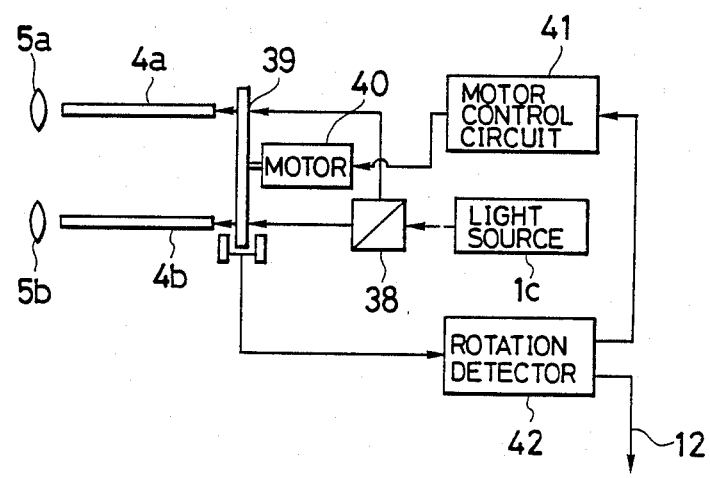
FIG. 5 is a view showing the construction of a modified embodiment of a device for switching the illuminated light.
Figure 6:
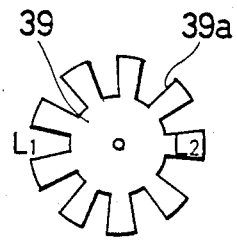
FIG. 6 is a front view showing an example of a turret used in the device for switching the illuminated light.

FIGS. 5 and 6 show a modified embodiment of the device for switching the illuminated light in which the device is mechanically constructed.

In FIG. 5, illuminating light from one light source 1c is divided into two sections by a beam splitter 38 which are respectively guided to incident ends of the light guides 4a and 4b. A turret 39 has a slit 39a for alternately passing and interrupting incident light towards both the light guides 4a and 4b as shown in FIG. 6. The apparatus further has a motor 40 for rotating the turret 39, a circuit 41 for controlling the operation of the motor 40, a detector 42 for detecting the rotation of the turret 39 and transmitting a synchronous signal to the control circuit 13 of FIG. 1.

When the turret 39 is rotated by the motor 40 through the control of the motor control circuit 41, as shown in FIG. 6, one of incident light sections $L_1$ and $L_2$ toward both the light guides 4a and 4b passes through the turret 39, the other thereof is interrupted by the turret 39, thereby alternately stereo-illuminating the light from the first and second illuminating lenses 5a and 5b to the inspected object.

In the embodiments mentioned above, the illuminating lenses as an illuminating means alternately illuminate to the inspected object by switching the illuminating light from two illuminating points different from each other, but more than three illuminating lenses may sequentially illuminate to the inspected object by switching the illuminating light in more than three illuminating points different from each other. In the case of the more than three illuminating points, the irregularity of the inspected object can be further exactly measured.

The endoscope mentioned above is constructed as an endoscope of a front viewing type, but may be constructed as an endoscope of a side viewing type in which a plurality of illuminating lenses, an objective lens, etc., are disposed on a side face of a scope end.

Figure 7:
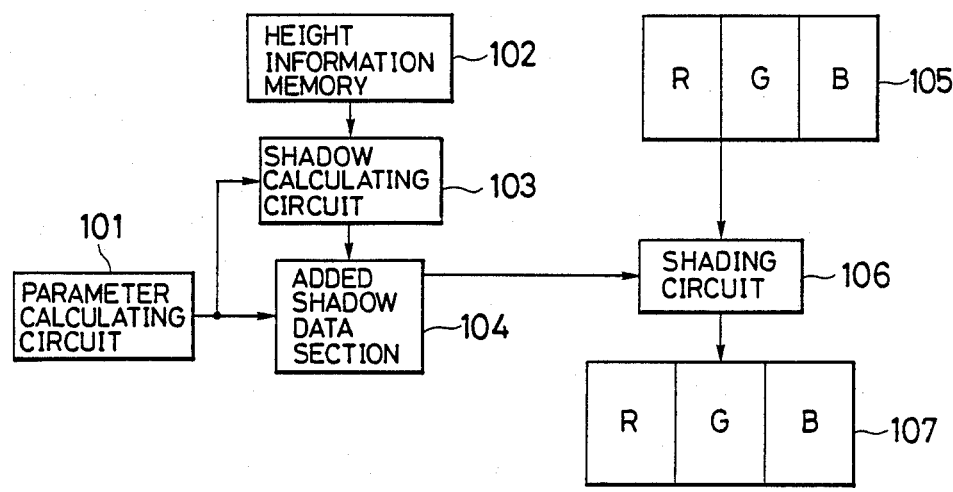
FIG. 7 is a block view showing a circuit for adding shadow to an image to strengthen the image in the endoscopic apparatus of the present invention.
Figure 8:
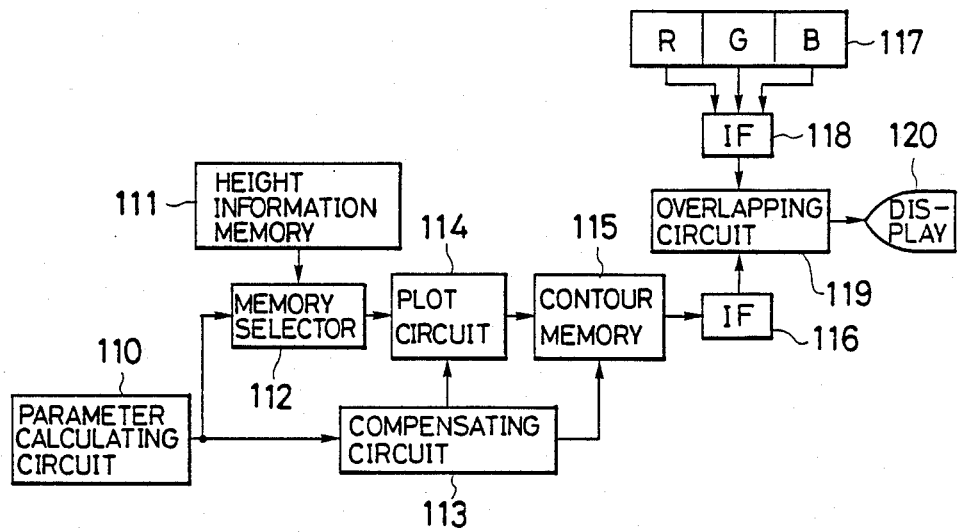
FIG. 8 is a block view showing a circuit for adding contour to the image to strengthen the image in the endoscopic apparatus of the present invention.

FIG. 7 is a block view showing a circuit for adding shadow to an image to strengthen the image in the endoscopic apparatus of the present invention. FIG. 8 is a block view showing a circuit for adding contour to the image to strengthen the image in the endoscopic apparatus of the present invention.

In FIG. 7, illuminating direction, position of light source, etc., as original parameters are inputted to a parameter calculating circuit 101. An output from the parameter calculating circuit 101, and an output from a height information memory 102 indicating height in irregularity of an inspected object are inputted to a shadow calculating circuit 103 for calculating shadow of the inspected object. An output from the shadow calculating circuit 103 is inputted to an added shadow data section 104 which outputs a signal based on a luminance signal for an image to a shading circuit 106. The shading circuit 106 also inputs red, green and blue (RGB) signals from an image memory 105, and outputs a signal indicative of the shading of the image to an image memory 107. According to the construction of FIG. 7, shadow is added to the normal image, thereby strengthening the image and improving the quality thereof.

In FIG. 8, height, etc., as original parameters are inputted to a parameter calculating circuit 110. An output signal from the parameter calculating circuit 110, and an output signal from a height information memory 111 for memorizing height of an inspected object are inputted to a memory selector 112. The output signal from the parameter calculating circuit 110 is also outputted to a compensating circuit 113 for compensating the output therefrom. A selected memory outputted from the memory selector 112, and a compensating signal from the compensating circuit 113 are inputted to a plot circuit 114 which outputs a signal for plotting the image to a contour memory 115. The contour memory 115 also inputs the compensating signal from the compensating circuit 113, and outputs a memory indicative of the contour of the image to an overlapping circuit 119 through an interface 116. The overlapping circuit 119 also input RGB signals from an image memory 117 through an interface 118. Thus, the output signal from the contour memory 115 and the RGB signals from the image memory 117 are overlapped in the overlapping circuit 119, thereby adding contour to the image and displaying the contoured image in the display section 120.

According to the construction of FIG. 8, contour is added to an image, and the quality of the image is improved.

As mentioned above, in accordance with the present invention, an inspected object is illuminated by sequentially switching light illuminated, using a plurality of illuminating means disposed around an observing point, from angular positions different from each other, and an image of the inspected object is picked up by an image pick-up means disposed at the observing point, thereby providing image information corresponding to the plural illuminating means with respect to the different positions. Further, the image information are processed by a processing unit, and height information with respect to the three-dimensional shape of the inspected object are outputted. Accordingly, the irregularity of the inspected object such as a diseased portion within a human's body can be exactly measured three-dimensionally, and can be displayed on a monitor, etc., at real time. Accordingly, the present invention can provide an endoscope greatly improving the diagnostic ability of the inspected object.

What is claimed is:

1. An endoscopic apparatus comprising:
   illuminating means disposed at an end of a scope and illuminating an inspected object by sequentially switching illuminating light from positions different from each other;
   means for picking up an image of the inspected object illuminated by the illuminating means; and
   means for processing image information outputted from the image pick-up means and corresponding to the respective positions of the illuminating means, said processing means outputting information with respect to the height in irregularity of the inspected object.

2. An endoscopic apparatus as claimed in claim 1, wherein the illuminating means is provided with a plurality of illuminating members disposed around an observing point.

3. An endoscopic apparatus as claimed in claim 2, wherein the inspected object is illuminated by sequentially switching the illuminating light from angles different from each other.

4. An endoscopic apparatus as claimed in claim 1, wherein the processing means outputs the information with respect to the height in irregularity of the inspected object having a three-dimensional shape at real time.

5. An endoscopic apparatus as claimed in claim 1, wherein the illuminating means is provided with first and second illuminating lenses, and the inspected object is illuminated by alternately switching the illuminated light from the first and second illuminated lenses.

6. An endoscopic apparatus as claimed in claim 5, wherein said apparatus further comprises a first image memory for memorizing first image data provided when the inspected object is illuminated by the first illuminating lens, and a second image memory for memorizing second image data provided when the inspected object is illuminated by the second illuminating lens.

7. An endoscopic apparatus as claimed in claim 6, wherein the first image data are shifted every picture element from the left to the right, and the second image data are shifted every picture element from the right to the left.

8. An endoscopic apparatus as claimed in claim 6, wherein said apparatus further comprises a circuit for cancelling an unbalance in light intensity of the image with respect to the right and left thereof based on outputs from the first and second image memories.

9. An endoscopic apparatus as claimed in claim 1, wherein the illuminating light from a light source is divided into plural sections, and said apparatus further comprises a plurality of light guides for receiving the plural light sections, and a turret for alternately passing and interrupting the incident light toward the light guides.

10. An endoscopic apparatus as claimed in claim 1, wherein said apparatus further comprises a circuit for adding shadow to the image to strengthen the image.

11. An endoscopic apparatus as claimed in claim 1, wherein said apparatus further comprises a circuit for adding contour to the image.

12. An endoscopic apparatus comprising:
    a plurality of illuminating means disposed at an end of a scope around an observing point and illuminating an inspected object by sequentially switching illuminating light from positions different from each other;
    image pick-up means disposed at the observing point and picking up an image of the inspected object illuminated by sequentially switching the plural illuminating means; and
    processing means for processing image information outputted from the image pick-up means and corresponding to the respective positions of the plural illuminating means, said processing means outputting information with respect to the height of the inspected object having a three-dimensional shape.

* * * * *